United States Patent [19]

Archer et al.

[11] Patent Number: 4,507,290

[45] Date of Patent: Mar. 26, 1985

[54] ESTERS OF 17 α-ETHYNYL 19-NOR-TESTOSTERONE AND 17 α-ETHYNYL-18-HOMO-19-NOR-TESTOSTERONE AND PHARMACEUTICAL COMPOSITIONS CONTAINING THE SAME

[75] Inventors: Sydney Archer, Troy, N.Y.; Giuseppe Benagiano, Rome, Italy; Pierre Crabbé, Paris, France; Egon Diczfalusy, Stockholm, Sweden; Carl Djerassi, Stanford, Calif.; Josef Fried, Chicago, Ill.

[73] Assignee: World Health Organization, Geneva, Switzerland

[21] Appl. No.: 251,914

[22] Filed: Apr. 7, 1981

[51] Int. Cl.³ .............................................. A61K 31/56

[52] U.S. Cl. ................................ 514/172; 260/397.4; 260/397.5; 514/179

[58] Field of Search ...................... 260/397.4; 424/243

[56] References Cited

U.S. PATENT DOCUMENTS

| | | | |
|---|---|---|---|
| 3,959,322 | 5/1976 | Hughes et al. | 260/397.4 |
| 4,027,019 | 5/1977 | Shroff | 260/397.4 |
| 4,089,952 | 5/1978 | Itil et al. | 424/243 |
| 4,119,626 | 10/1978 | Schulze et al. | 260/397.4 |
| 4,181,721 | 1/1980 | Speck et al. | 424/243 |

Primary Examiner—Elbert L. Roberts
Attorney, Agent, or Firm—Cushman, Darby & Cushman

[57] ABSTRACT

Esters of 17 α-ethynyl 19-nor-testosterone and 17 α-ethynyl-18-homo-19-nor-testosterone and the 3-oximes thereof having long-active contraceptive activity.

21 Claims, No Drawings

ESTERS OF 17 α-ETHYNYL 19-NOR-TESTOSTERONE AND 17 α-ETHYNYL-18-HOMO-19-NOR-TESTOSTERONE AND PHARMACEUTICAL COMPOSITIONS CONTAINING THE SAME

BACKGROUND AND SUMMARY OF THE INVENTION

Heretofore, active steroid type contraceptive agents included such material as 17 α-hydroxyprogestrone, norethisterone (norethynyl testosterone, NET) and levonorgestrel. Subsequently the art developed, as long acting injectable steroid type contraceptives, depo-medroxyprogesterone acetate (Depo-Provera) and norethisterone enanthate (NET enanthate), these latter two agents providing some sustained-release advantages over the earilier known contraceptive agents.

It has now been found that certain other novel steroid esters exhibit improved sustained release characteristics when administered to a human, particularly a female, as an injectable contraceptive or fertility suppressing agent.

The novel steroid esters of the present invention are selected from the group consisting of (a) an ester of D-17 α-ethynyl-19-nortestosterone having the following formula

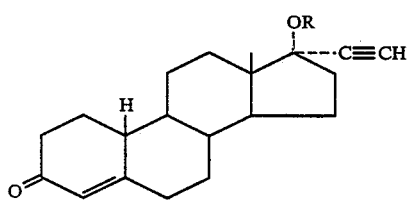

wherein R is selected from the group consisting of (1)

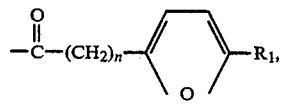

wherein $R_1$ is lower alkyl, preferably methyl or ethyl and n is 1-6, and (2) acyl derived from an alicyclic carboxylic acid wherein the alicyclic moiety can have 3-8 carbon atoms in the ring, the ring being substituted by alkyl having 1-8 carbon atoms and preferably by methyl or ethyl;

(b) the corresponding oxime of the ester defined in (a);

(c) an ester of levo-norgestrel, i.e., d(+) norgestrel having the formula

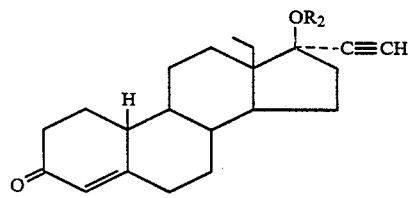

wherein $R_2$ is acyl derived from an alicyclic carboxylic acid wherein the alicyclic moiety can have 3-6, preferably 3 and 4, carbon atoms in the ring;

(d) the corresponding oxime of the ester defined in (c);

(e) an ester of levo-norgestrel having the formula (II) above, wherein $R_2$ is acyl derived from an aliphatic carboxylic acid containing 5 carbon atoms, in extenso pentanoic acid isomers, i.e.

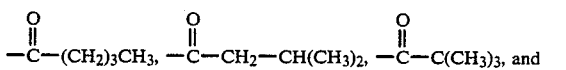

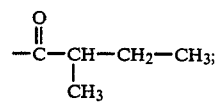

(f) the corresponding oxime of the ester defined in (e);

(g) an ester of levo-norgestrel having the formula (II) above, wherein $R_2$ is an acyl derived from an aliphatic carboxylic acid containing 3 and 4 carbon aoms, i.e., propionic acid and butyric acid isomers;

(h) the corresponding oxime of the ester defined in (g); and (i) an ester of levo-norgestrel having the formula (II) above, wherein $R_2$ is an acyl chain as defined in (a).

Representative steroid esters defined in (a) (1) and (i) above are those produced by the esterification of D-17 α-ethynyl-19-nortesterone and levo-norgestrel with a β-(5-lower alkylene-2 furyl) lower alkanoic acid, preferably a propanoic acid derivative, wherein the 5-lower alkylene substituent, i.e. —(CH₂)n has 1-6 carbon atoms and preferably is methyl or ethyl. Examples of preferred acids include β-(5-methyl-2-furyl) propionic acid and β-(5-ethyl-2-furyl) propionic acid. With these preferred acids, R in Formula I and Formula II can be defined as

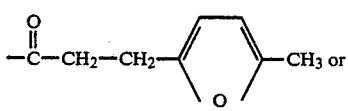

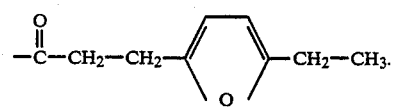

Representative steroid esters defined in (a) (2) above are those produced by the esterification of D-17 α-ethynyl-19-nortesterone and an alicyclic carboxylic acid wherein the alicyclic moiety has 3-8 carbon atoms in the ring. The ring is also substituted by alkyl having 1-8 carbon atoms, this alkyl substituent being either in the cis or trans configuration, the trans configuration being preferred. In these alicyclic carboxylic acids, the ring is preferably cyclohexyl, although certainly it can also be, for instance cyclopentyl or cycloheptyl. Thus, in Formula I, above, R can be defined as

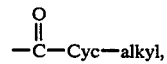

wherein Cyc is a cycloalkyl ring having 3-8 carbon atoms and the alkyl substituent, in the cis or trans configuration, has 1-8 carbon atoms. Preferably, then, R can be defined as

or more preferably as

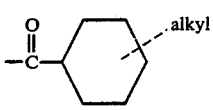

wherein — alkyl and - - - alkyl represent, respectively, the cis and trans configuration of the alkyl substituent. When the more preferred acids, i.e. trans-4-methylcyclohexane carboxylic acid and trans-4-ethylcyclohexane carboxylic acids are employed, R in Formula I can be defined as

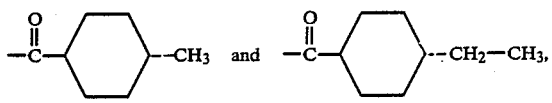

respectively.

Representative steroid esters defined in (c) above are those produced by the esterification of levo-norgestrel and an alicyclic carboxylic acid wherein the alicyclic moiety has 3-6, and preferably 3 and 4, carbon atoms. Thus in Formula II, above, $R_2$ can be defined as

wherein Cyc is a cycloalkyl ring having 3-6 carbon atoms. Preferably then, $R_2$ can be defined as

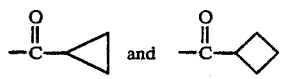

when cyclopropane and cyclobutane carboxylic acid are employed in the esterification reaction.

Representative steroid esters defined in (e) above are those produced by the esterification of levo-norgestrel and an aliphatic carboxylic acid wherein the aliphatic moiety has four and five carbon atoms. Thus in formula (II) above, $R_2$ can be defined as

$-(CH_2)_2CH_3$, $-(CH_2)_3-CH_3$, $-C-(CH_3)_3$,

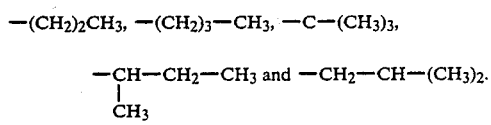

The novel steroid esters of this invention can be prepared, for instance, by esterifying the D-17 α-ethynyl-19-nortesterone with the organic carboxylic acid in the presence of benzene sulphonyl chloride, as the coupling agent.

Generally, an equimolar ratio of carboxylic acid:benzene sulphonyl chloride is employed. The organic acid, dissolved in pyridine, is reacted with a molar equivalent of benzene sulphonyl chloride and the resulting mixture is left to stand at ambient temperature for a period of time sufficient to provide the corresponding anhydride.

Thereafter the D-17 α-ethynyl-19-nortesterone, dissolved in pyridine, is added and the reaction is monitored by thin layer chromatography.

At the completion of the reaction, the reaction mixture is poured onto ice and extracted with chloroform. The chloroform layer is washed several times with dilute HCl, water, aqueous sodium carbonate and finally with water.

The resulting organic layer is dried using anhydrous sodium sulfate, filtered and thereafter the solvent is evaporated. The resulting residue can then be subjected to IR, UV and NMR analysis and either recrystallized or separated by TLC to yield pure compounds.

Alternatively, the novel steroid esters of this invention can also be prepared by esterifying levo-norgestrel with the organic carboxylic acid in the presence of trifluoroacetic acid anhydride in anhydrous benzene solution.

Several other methods are available for the preparation of the steroid esters of the present invention. These other methods often require the protection of the 3-keto function (see J. Chem. Soc. 1963, 3578, Evans et al), the activation of the 17-hydroxy group via a lithium salt (see J. Org. Chem., 1970, 35, 1198, Kaiser et al) or a thallium salt (see Synth. Comm. 1977, 7, 383, Herz et al) and conversion of the carboxylic acid into the more reactive chloride (see J.A.C.S. 1957, 79, 4472, Gould et al, Herz et al supra or Kaiser et al supra), or anhydride (see Canad. J. Chem., 1968, 46, 351, Crabbé et al).

Specifically, using a thallous salt, the following esterification procedure can be employed.

To a solution of 8.95 g (0.03 mol) of D-17α-ethynyl-19-nortesterone in 100 ml of dry benzene, there are added, with stirring, 2.3 ml (0.033 mol) of thallous ethoxide. Although the benzene distills off slowly, the volume of the reaction mixture is maintained at about 100 ml by the dropwise addition of dry benzene thereto. After 200 ml of benzene have been distilled off, the reaction mixture is cooled in an ice-water bath and the carboxylic acid, in acyl halide form (0.036 mol), is added dropwise thereto. The resulting mixture is refluxed for 5 hours and thereafter cooled and filtered through a bed of kieselguhr. The resulting precipitate is washed with 20 ml of benzene, five times and the solvent then evaporated. The resulting residue is then purified by column chromatography (silica gel) using a 20:80 mixture of chloroform and petroleum ether as the eluant. Alternatively, the residue can be purified by HPLC (silica gel) using a 1:1 mixture of chloroform and n-hexane as the eluant and collecting the main first peak. Still another purification operation can be effected using TLC (silica gel) with a 95:5 mixture of chloroform and ethyl acetate as the eluant. The ester yield, in accordance with this procedure, is about 70 to 90%.

The above thallous ethoxide method can also be employed in the esterification of levo-norgestrel. The only difference is that the ratio of levo-norgestrel:thallous ethoxide:acyl halide is 1:1.2:1.3 moles. The ester yield is about 60–80% using purification methods similar to those described above.

The following non-limiting specific examples illustrate the present invention.

EXAMPLE 1

A 19-norethisterone ester having the following formula

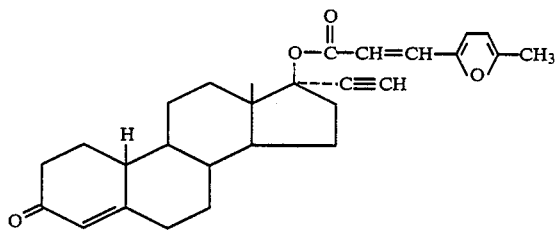

is prepared as follows:

An equimolar mixture of benzene sulphonyl chloride (0.05 mol) and δ-(5-methyl-2-furfuryl) acrylic acid (0.05 mol) in anhydrous pyridine (15 ml) were left at room temperature for 1 hour. A heavy anhydride layer separated out. 0.05 mol of 19-norethisterone in pyridine (15 ml) was added thereto. On completion of the reaction (48 hours) followed by thin layer chromatography the above ester in a 55% yield was obtained.

The β-(5-methyl-2-furfuryl) acrylic acid can be prepared as follows:

20 g of distilled 5-methylfurfurylaldehyde, 21.6 g of malonic acid and 10.5 ml of pyridine were heated at a temperature of 80°–90° C. on a water bath for 3 hours. After cooling to ambient temperature, 100 ml of 10% (v/v) HCl were added to the resulting crystalline residue. The product was then filtered, washed and dried in a desiccator. The resulting off-white product, on crystallization from aqueous methanol, yielded 22.7 g (82%) of β-(5-methyl-2-furyl) acrylic acid, the melting point being 155°–157° C.

EXAMPLE 2

The procedures of Example 1 are repeated using instead β-(5-methyl-2-furyl) propionic acid to produce an ester having the formula

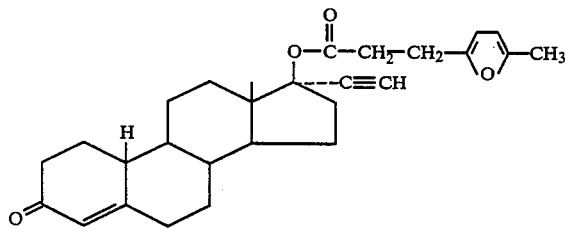

The β-(5-methyl-2-furyl) propionic acid can be prepared as follows:

14.6 g of β-(5-methyl-2-furyl) acrylic acid, prepared in accordance with the procedures of Example 1, were dissolved in 100 ml H₂O containing 4 g of NaOH. 10 g of Raney nickel alloy were then added. The resulting suspension was stirred in an ice-bath and a solution of 8 g of NaOH and 30 ml H₂O was slowly added to the stirred solution, while the temperature thereof is maintained at below 20° C. On completion of the addition of the NaOH to the reaction mixture the temperature was permitted to rise slowly to 30° C. The reaction mixture was maintained at this temperature for 2 hours. Thereafter the reaction mixture was filtered with the filtrate being acidified with diluted HCl and extracted with ethyl acetate. The resulting extract was washed with water until neutral, dried and evaporated. The residue, on recrystallization from petroleum ether (boiling point—40°–60° C.), yielded 6.7 g (45% yield) of β-(5-methyl-2-furyl) propionic acid. Chromatography on the mother liquor on a column of silica gel and eluting with petroleum ether (boiling point—40°–60° C.) gave a further yield of 2.5 g (17%) of the pure acid melting at 56°–58° C.

EXAMPLE 3

The procedures of Example 1 are repeated using instead of the one hand cis-4-methylcyclohexane carboxylic acid, and on the other hand, trans-4-methylcyclohexane carboxylic acid to produce esters having, respectively, the following formulae:

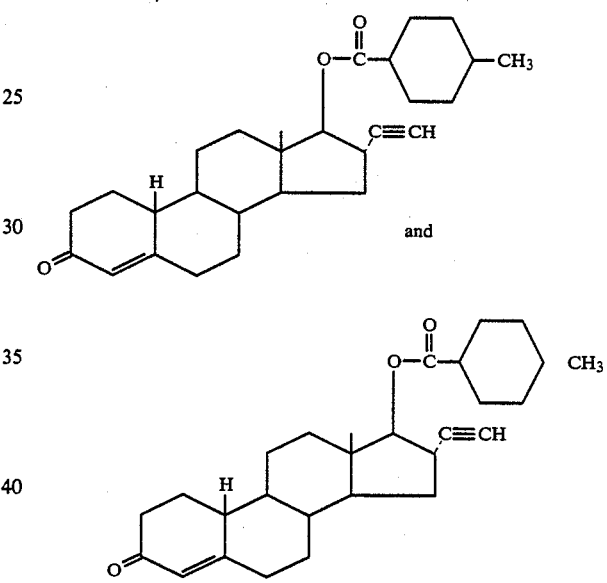

The cis-4-methylcyclohexane carboxylic acid employed in the esterification reaction was produced in the following manner:

A solution of 20 g of p-toluic acid,

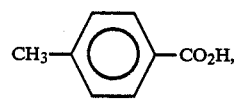

in 200 ml of acetic acid was hydrogenated in the presence of 0.4 g of PtO₂ at 50 psi until the uptake of hydrogen was complete. The solution was then evaporated to provide a mixture of cis and trans 4-methylcyclohexane carboxylic acid; boiling point—124°–126° C. (20 min), predominantly cis. Esterification of the mixed acids with methanol-sulfuric acid provided a mixture of cis and trans methyl 4-methylcyclohexane carboxylate; boiling point—79°–80° C. (20 min), predominantly cis. This ester mixture was separated by HPLC (water, Prep LC System 500) with a double column (silica gel) using n-hexane/chloroform (80:20) as eluant (cahrt speed 5 min/cm, flow rate 0.2 l/min). The fast moving fraction (retention time, 10 min) was pure cis methyl cyclohexane carboxylate (NMR had only one peak for the methyl ester at 218 cps, Varian T-60, internal TMS). The slow moving fraction (retention time, 12 min) was pure trans-methyl-4-methyl cyclohexane carboxylate (NMR had only one peak for the methyl ester at 216 cps). The ratio of cis to trans esters separated was 7 to 3.

The cis ester was then hydrolyzed with dilute NaOH and the resulting acid was crystallized from petroleum ether to give cis-4-methyl cyclohexane carboxylic acid, melting point—31°-32° C. (F. R. Jensen et al, J.A.C.S., 90, 5793, 1968, M.P. 31.2-31.4).

The trans 4-methyl cyclohexane carboxylic acid, used in the above esterification was produced as follows.

a solution of p-toluic acid was hydrogenated in the manner outlined above. The resulting mixture of acids was esterified with ethanol-sulfuric acid to provide a mixture of cis and trans ethyl 4-methyl cyclohexane carboxylate, melting point—86°-88° C. (20 min), the ratio of cis to trans being 7:3.

To a solution of 22 g of sodium in 500 ml of absolute ethanol, 20 g of the above mixed esters were added and refluxed for 7 days. 100 ml of water were then added and refluxing was continued for an additional day. The solvent was evaporated and the residue was dissolved in water and acidified with diluted HCl. The resulting mixture was extracted with chloroform. The solvent was then evaporated and the residue was crystallized from petroleum ether to provide trans 4-methyl cyclohexane carboxylic acid (80% overall yield), melting point=112°-113° C. (F. R. Jensen et al, J.A.C.S., 90, 5793, 1968, melting point=110.7°-111.9° C.).

EXAMPLE 4

The procedures of Example 1 are repeated using instead trans-4-ethylcyclohexane carboxylic acid to provide an ester having the formula

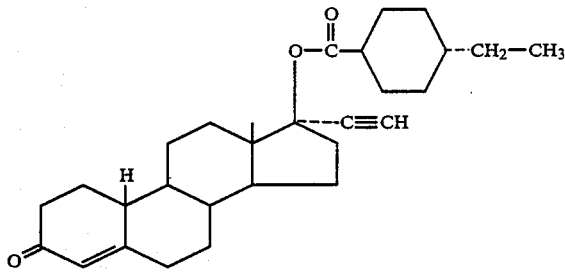

The trans-4-ethylcyclohexane carboxylic acid used above was prepared as follows.

A solution of 20 g of p-ethylbenzoic acid in 200 ml of acetic acid was hydrogenated in the presence of PtO₂ at 50 psi. At the end of the reaction the catalyst was filtered off and the solvent was evaporated. The residue, a mixture of cis and trans 4-ethyl cyclohexane carboxylic acids, was esterified with ethanol-sulfuric acid to provide a mixture of cis and trans ethyl 4-ethyl cyclohexane carboxylate, boiling point—102°-104° C. (4 mn). Isomerization and hydrolysis of this mixture were carried out essentially as described in Example 3 and the resulting trans acid was crystallized from petroleum ether—melting point=49°-50° C. (Allinger et al, J. Org. Chem. 31, 894, 1966, melting point=49°-49.8° C.). The overall yield is 80%.

EXAMPLE 5

To a solution of levo-norgestrel (0.03 mol) in 100 ml of dry benzene there is added thallous ethoxide (0.036 mol). The benzene is distilled off slowly but the volume of the reaction mixture is maintained at about 100 ml by the dropwise addition of dry benzene thereto. After 200 ml of the benzene are distilled off, the reaction mixture is cooled in an ice water bath. Thereafter 0.039 mol of cyclobutane carboxylic acid, in its acyl chloride form, is added dropwise to the reaction mixture which is then refluxed for 5 hours. After cooling, the reaction mixture is filtered through a bed of kieselguhr and the resulting precipitate is washed five times with 20 ml of benzene. The solvent is then evaporated and the resulting residue is purified in accordance with conventional procedures. The resulting ester has the formula

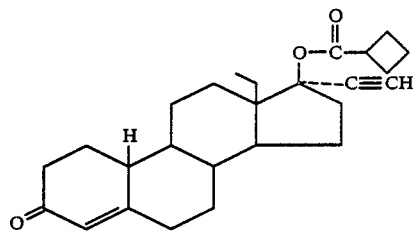

Alternatively, trifluoroacetic anhydride (13 ml=19.33 g, 92.03 mM) and cyclobutane carboxylic acid (8.0 ml=8.37 g, 83.60 mM, freshly distilled) were dissolved in benzene (240 ml) and stirred under anhydrous conditions for 30 minutes. Levo-norgestrel (15 g, 48.00 mM) was then added and the solution was stirred at room temperature for 40 minutes. The reaction mixture was then diluted with ice water and extracted with ether. The ether extract was washed with saturated sodium bicarbonate solution (2X), water (2X) and brine (1X), dried (Na₂SO₄), filered, and concentrated in vacuo. The residue was then dissolved in acetone and an equal volume of hexane was added to it. Crystallization took place when it was set aside, yielding 10.5 g of the above-identified ester having a melting point of 226°-228° C.

The biological assay employed for assessment of the long-acting activity of the novel steroid esters of the present invention is the suppression of cornification in adult cycling rats. Under normal conditions these rats exhibit a vaginal cornification cycle of 4–5 days. Single injection of a long-acting progestin suppresses the cyclical appearance of cornified cells. The esters of this invention as well as known contraceptive agents, i.e. depo-medroxyprogesterone acetate (DMPA) and norethisterone enanthate (NET ENT) are administered at the dose of 16 mg/rat and subsequently the rats are smeared on a daily basis. The end point is the appearance of cornified smears which indicates that the contraceptive agent no longer inhibits the pituitary-ovarian axes. It has been found that the novel steroid esters of the present invention exhibit essentially as good as or better long-acting activity than known contraceptive agents.

The novel steroid esters of this invention can be employed in admixture with conventional excipients, i.e. pharmaceutically acceptable organic or inorganic carrier substances suitable for parenteral application which substances do not deleteriously react with these steroid esters. Particularly suitable are solutions, oily or aqueous solutions, as well as suspensions, i.e., oily or aqueous suspensions using appropriate particle sizes. Generally the novel steroids of this invention are administered by subcutaneous injection in unit dosage forms the amount per unit dosage being about 100 mg to 200 mg, preferably about 120 mg to 180 mg of the steroid ester of this invention.

This invention is also related to the 3-oxime derivatives of the above-defined esters which can be prepared by reaction of the 3-keto steroids with 1.5 to 2 equivalents of hydroxylamine hydrochloride in ethanol solution (in the presence of a few drops of pyridine), at reflux temperature for one hour, thus affording the corresponding 3-oximes.

EXAMPLE 6

The oxime derivative of norgestrel cyclobutyl-carboxylate, produced in Example 5 was prepared by reacting said ester with hydroxylamine hydrochloride in pyridine in accordance with the following reaction scheme:

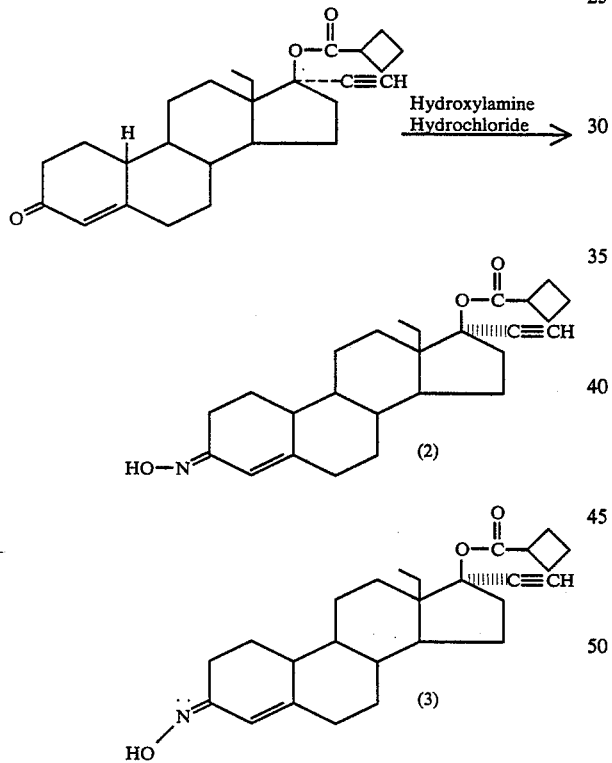

A mixture of anti (2) and syn (3) isomers was obtained in approximately 3:2 ratio as shown by high pressure liquid chromatography. After dry column chromatography the product was crystallized from ether to give both isomers in the same ratio. The ether was removed by prolonged heating under high vacuum for several days. A total of 2.51 g of pure oxime, (2)+(3) was prepared from 4.5 g of the norgestrel 17β-cyclobutylcarboxylate (54%), initial reactant. This reaction is described in detail below.

Hydroxylamine hydrochloride (4.0 g, 57.55 mM) was added to a stirred solution of norgestrel 17 β-cyclobutyl-carboxylate (4.5 g, 11.40 mM) in pyridine (40 ml, distilled from BaO). The reaction mixture was stirred at 100° C. for 6 minutes under anhydrous conditions, and then cooled in an ice bath. Hydrochloric acid (1N, 340 ml) was added dropwise with stirring. The product separated out as a white oil. The mixture was extracted with ethyl acetate and washed with 0.5N HCL (1X), water 1X) saturated sodium bicarbonate solution (1X), water (2X) and brine. The organic extract was dried over sodium sulfate, filtered and concentrated in vacuo. The resulting oxime, (2)+(3) was purified by dry column chromatography using ether:hexanes (2:1) as the eluting solvent. Crystallization from ether gave the oxime, (2)+(3), as a solid (1.90 g—m.p. 185°–187° C.). The mother liquors of crystallization were again purified by dry column chromatography and the material obtained from the column was crystallized from ether, yielding an additional 0.61 g of the oxime, (2)+(3). The ether used for crystallization was removed in about 80 hours with heat (80° C.) and high vacuum ($10^5$ mm Hg).

EXAMPLE 7

Norgestrel cyclopropyl carboxylate was prepared by the action of a mixture of trifluoroacetic anhydride and cyclopropane carboxylic acid or norgestrel in accordance with the following reaction scheme:

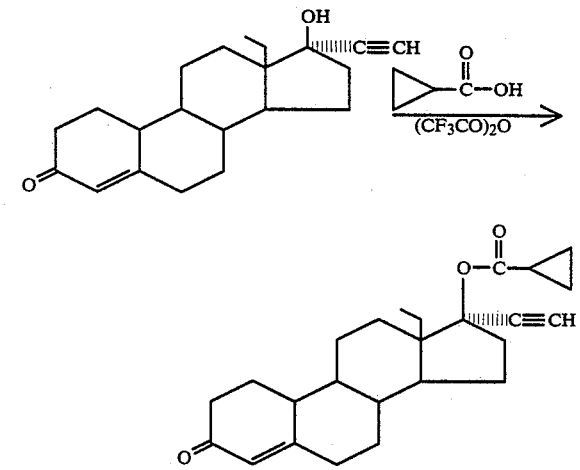

A solution of 14.4 ml trifluoroacetic anhydride (21.4 g–101.41 mM), 8.6 ml cyclopropane carboxylic acid (9.35 g–108.60 mM) and 240 ml benzene was stirred under anhydrous conditions at room temperature for 30 minutes. 1.15 g (−)-norgestrel (48.00 mM) were added and the solution was stirred at ambient temperature for 1 hour 10 minutes. The reaction mixture was diluted with water and extracted with ether. The ether extract was washed with water (1x), saturated sodium bicarbonate solution (2x), water (2x), and brine, then dried ($Na_2SO_4$), filtered and concentrated in vacuo. Ether was evaporated to obtain the residue which was dried under high vacuum. It became a foam. The procedure was repeated until the foam was free from other impurities (checked by TLC and HPLC), yielding 10.2 g of the desired norgestrel cyclopropyl carboxylate having a melting point of 232°–235° C.

EXAMPLE 8

The oxime derivative of norgestrel cyclopropyl carboxylate, produced in Example 7, was prepared by reacting said ester with hydroxylamine hydrochloride in pyridine in accordance with the following reaction scheme:

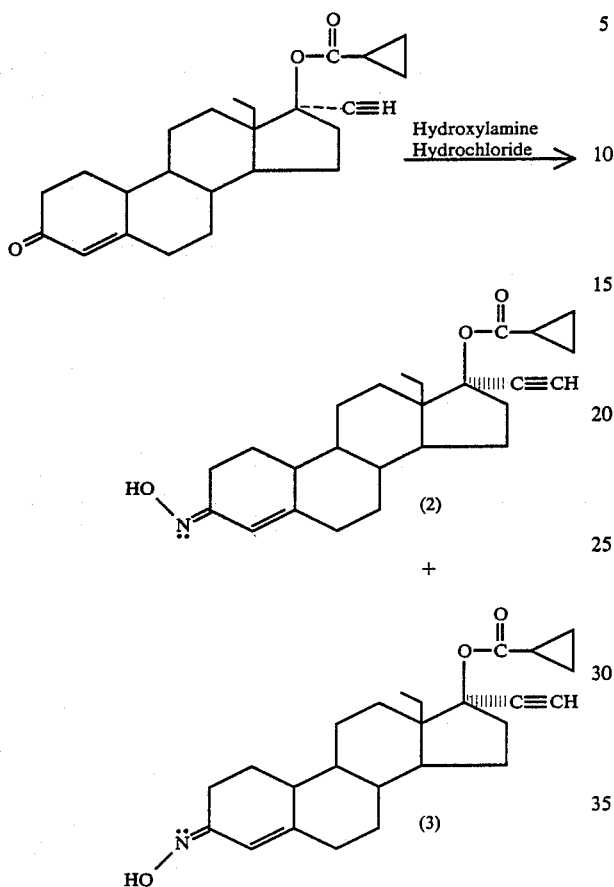

To a stirred solution of 4.6 g norgestrel 17-cyclopropyl carboxylate (12.08 mM) in 40 ml of pyridine there were added 4.2 g of hydroxylamine hydrochloride (60.44 mM). The reaction mixture was heated at 100° C. for 6 minutes, then cooled in an ice bath. 363 ml of 1N HCl were added slowly with stirring. The product separated out as a white oil. The mixture was extracted with ethyl acetate and washed with water (1x), HCl (0.5N), water (2x) and brine (1x). The organic extract was dried (Na$_2$SO$_4$), filtered, and concentrated in vacuo. Purification by dry column chromatography using ether:hexanes by dry column chromatography using ether:hexanes (2:1) as the eluting solvent gave the oxime (2+3, 4.3g) as a foam. The ratio of the syn (3) and anti (2) isomers was approximately 2:3 as determined by high pressure liquid chromatography (µPorasli column—heptane:2-propanol; 97:3). The foam was dissolved in ether and filtered to remove any particulate matter. Minute traces of solvent were removed by heating at 80° C. and at low pressure (10$^{-5}$ mm Hg) for several days, i.e. about 80 hours. The yield was 90%.

What is claimed is:

1. A steroid ester selected from the group consisting of
   (a) an ester of D-17α-ethynyl-19-nortestosterone having the formula

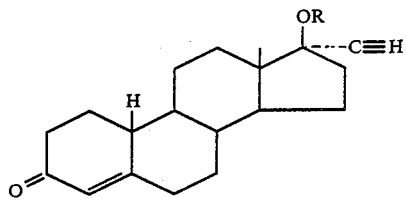

wherein R is selected from the group consisting of
(1)

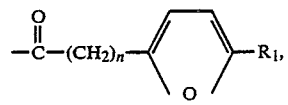

wherein R$_1$ is lower alkyl and n is 1-6, and
(2) acyl derived from an alicyclic carboxylic acid wherein the alicyclic moiety has 3-8 carbon atoms in the ring, said ring being substituted by alkyl having 1-8 carbon atoms;
(b) the corresponding oxime of the ester defined in (a);
(c) an ester of levo-norgestrel having the formula

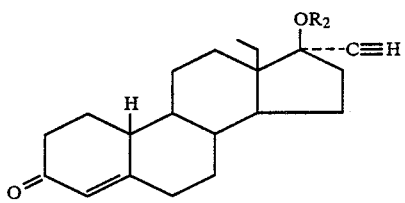

wherein R$_2$ is selected from the group consisting of
(i)

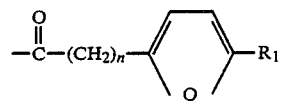

wherein R$_1$ is lower alkyl and n is 1-6, and (ii) acyl derived from an alicyclic carboxylic acid wherein the alicyclic moiety has 3-6 carbon atoms in the ring;
(d) the corresponding oxime of the ester defined in (c);
(e) and the oxime of an ester of levo-norgestrel having the formula in (c) wherein R$_2$ is acyl derived from an aliphatic carboxylic acid containing 4 or 5 carbon atoms.

2. The steroid ester of claim 1 wherein (a) (1) R is the residue of a β-(5-lower alkylene-2-furyl) lower alkanoic acid.

3. The steroid ester of claim 1 wherein (a) (1) R is

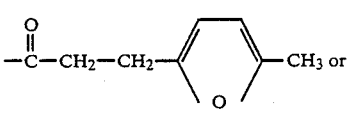

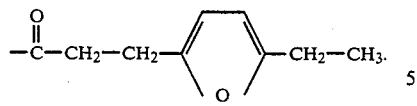

4. The steroid ester of claim 1 wherein (a) (2) R is

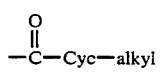

wherein Cyc is cycloalkyl having 3–8 carbon atoms and said alkyl in the cis or trans configuration has 1–8 carbon atoms.

5. The steroid ester of claim 1 wherein (a) (2) R is

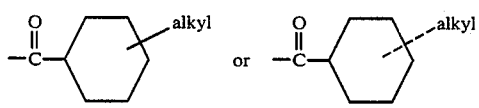

—alkyl and - - - alkyl representing respectively the cis and trans configurations of said alkyl substituent.

6. The steroid ester of claim 1 wherein (a) (2) R is

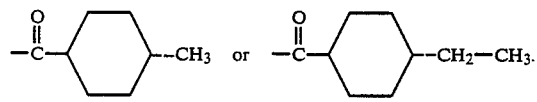

7. The steroid ester of claim 1 wherein (c) $R_2$ is

wherein Cyc is cycloalkyl having 3–6 carbon atoms.

8. The steroid ester of claim 1 wherein (e) $R_2$ is

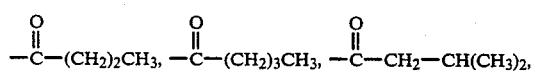

9. An ester of D-17 α-ethynyl-19-nortestosterone having the formula

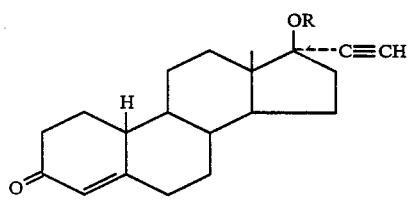

wherein R is selected from the group consisting of

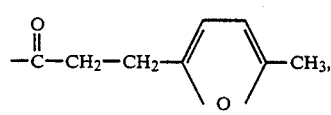 (1)

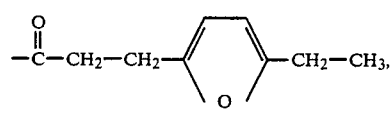 (2)

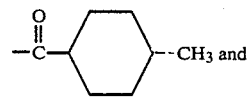 (3)

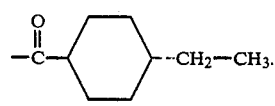 (4)

10. A ester of D-17 α-ethynyl-19-nortestosterone having the formula

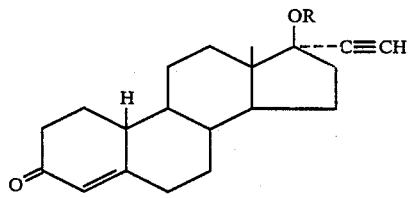

wherein R is

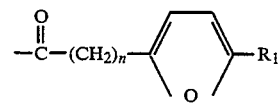

wherein $R_1$ is lower alkyl and n is 1–6.

11. The ester of claim 10 wherein R is

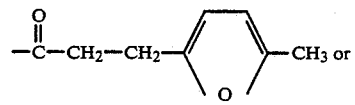 or

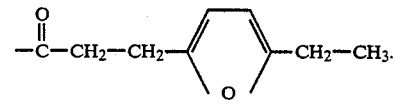

12. An ester of D-17 α-ethynyl-19-nortestosterone having the formula

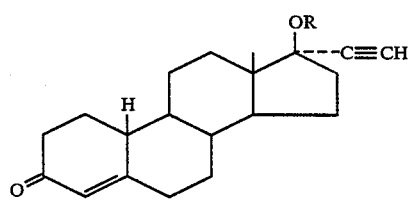

wherein R is acyl derived from an alicyclic carboxylic acid wherein the alicyclic moiety has 3–10 carbon atoms in the ring, said ring being substituted by alkyl having 1–8 carbon atoms.

13. The ester of claim 12 wherein R is

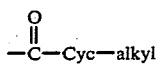

wherein Cyc is cycloalkyl having 3-8 carbon atoms and said alkyl is the cis and trans configuration.

14. The ester of claim 12 wherein R is

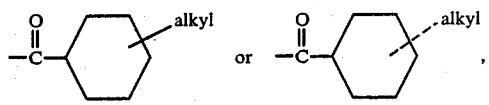

—alkyl and - - - alkyl representing respectively the cis and trans configurations of said alkyl.

15. The ester of claim 12 wherein R is

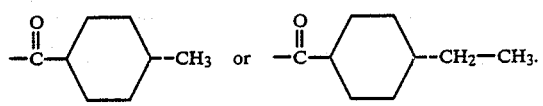

16. An ester of levo-norgestrel having the formula

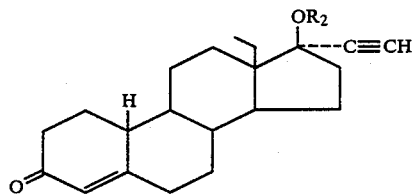

wherein $R_2$ is selected from the group consisting of (i)

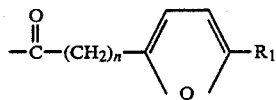

wherein $R_1$ is lower akyl and n is 1-5, and (ii) acyl derived from an alicyclic carboxylic acid wherein the alicyclic moiety has 3-6 carbon atoms in the ring.

17. A steroid ester selected from the group consisting of (a) an ester of D-17 α-ethynyl-19-nor testosterone having the formula

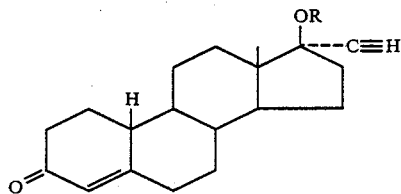

wherein R is

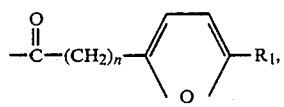

wherein $R_1$ is lower akyl and n is 1-6, (b) the corresponding oxime of the ester defined in (a);

(c) an ester of levo-norgestrel having the formula

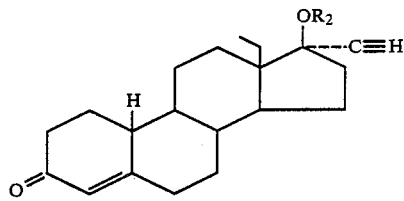

wherein $R_2$ is

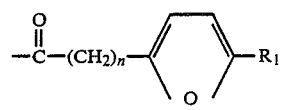

wherein $R_1$ is lower alkyl and n is 1-6; and (d) the corresponding oxime of the ester defined in (c).

18. A pharmaceutical composition for suppressing fertility comprising a fertility suppressing amount of a steroid ester in combination with a pharmaceutically acceptable carrier, said steroid ester being selected from the group consisting of (a) an ester of D-17-α-ethynyl-19-nortestosterone having the formula

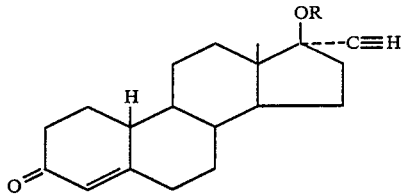

wherein R is selected from the group consisting of (1)

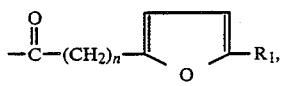

wherein $R_1$ is lower alkyl and n is 1-6, and (2) acyl derived from an alicyclic carboxylic acid wherein the alicyclic moiety has 3-8 carbon atoms in the ring, said ring being substituted by alkyl having 1-8 carbon atoms;

(b) the corresponding oxime of the ester defined in (a);

(c) an ester of levo-norgestrel having the formula

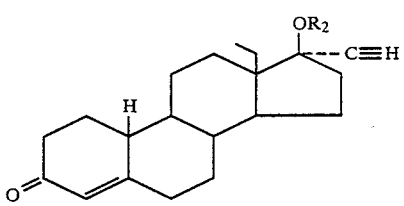

wherein $R_2$ is selected from the group consisting of (i)

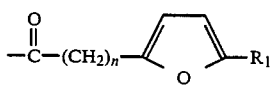

wherein $R_1$ is lower alkyl and n is 1-6, and
(ii) acyl derived from an alicyclic carboxylic acid wherein the alicyclic moiety has 3-6 carbon atoms in the ring;
(d) the corresponding oxime of the ester defined in (c); and
(e) the oxime of an ester of levo-norgestrel having the formula in (c) wherein $R_2$ is acyl derived from an aliphatic carboxylic acid containing 4 or 5 carbon atoms.

19. The pharmaceutical composition of claim 18 wherein said carrier is an oily or aqueous solution, or an oily or aqueous suspension using appropriate particle and crystal sizes.

20. An injectable therapeutic composition exhibiting sustained release contraceptive activity comprising a steroid ester in an amount of 100 to 200 mg in admixture with a pharmaceutically acceptable carrier, said steroid ester being selected from the group consisting of
(a) an ester of D-17-α-ethynyl-19-nortestosterone having the formula

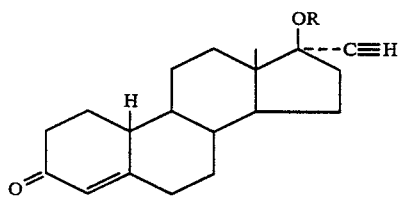

wherein R is selected from the group consisting of

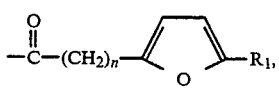

wherein $R_1$ is lower alkyl and n is 1-6, and
(2) acyl derived from an alicyclic carboxylic acid wherein the alicyclic moiety has 3-8 carbon atoms in the ring, said ring being substituted by alkyl having 1-8 carbon atoms;
(b) the corresponding oxime of the ester defined in (a);
(c) an ester of levo-norgestrel having the formula

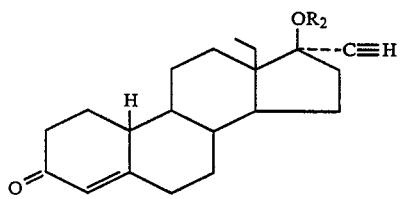

wherein $R_2$ is selected from the group consisting of
(i)

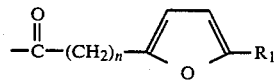

wherein $R_1$ is lower alkyl and n is 1-6, and
(ii) acyl derived from an alicyclic carboxylic acid wherein the alicyclic moiety has 3-6 carbon atoms in the ring;
(d) the corresponding oxime of the ester defined in (c); and
(e) the oxime of an ester of levo-norgestrel having the formula in (c) wherein $R_2$ is acyl derived from an aliphatic carboxylic acid containing 4 or 5 carbon atoms.

21. A method of suppressing fertility comprising administering to a human a fertility suppressing amount of a steroid ester selected from the group consisting of
(a) an ester of D-17-α-ethynyl-19-nortestosterone having the formula

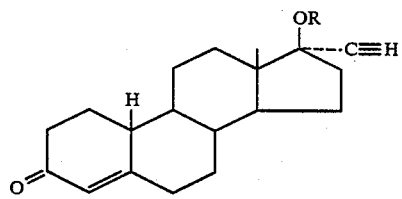

wherein R is selected from the group consisting of

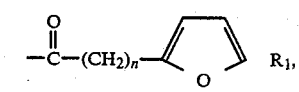

wherein $R_1$ is lower alkyl and n is 1-6, and
(2) acyl derived from an alicyclic carboxylic acid wherein the alicyclic moiety has 3-8 carbon atoms in the ring, said ring being substituted by alkyl having 1-8 carbon atoms;
(b) the corresponding oxime of the ester defined in (a);
(c) an ester of levo-norgestrel having the formula

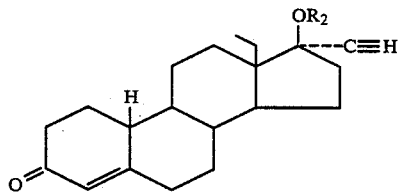

wherein $R_2$ is selected from the group consisting of
(i)

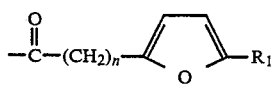

wherein $R_1$ is lower akyl and n is 1-6, and
(ii) acyl derived from an alicyclic carboxylic acid wherein the alicyclic moiety has 3-6 carbon atoms in the ring;
(d) the corresponding oxime of the ester defined in (c); and
(e) the oxime of an ester of levo-norgestrel having the formula in (c), wherein $R_2$ is acyl derived from an aliphatic carboxylic acid containing 4 or 5 carbon atoms.

* * * * *

UNITED STATES PATENT AND TRADEMARK OFFICE
CERTIFICATE OF CORRECTION

PATENT NO. : 4,507,290

DATED : March 26, 1985

INVENTOR(S) : Sydney Archer et al.

It is certified that error appears in the above—identified patent and that said Letters Patent is hereby corrected as shown below:

Col. 6, between lines 20 and 45, the structural formulas should read

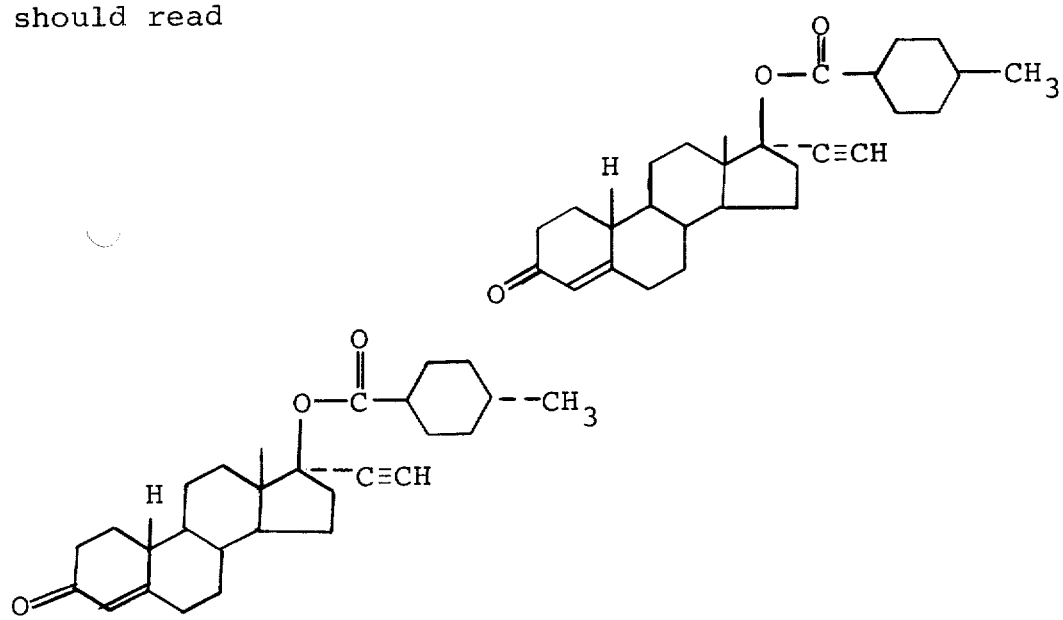

Signed and Sealed this

Tenth Day of December 1985

[SEAL]

Attest:

DONALD J. QUIGG

Attesting Officer

Commissioner of Patents and Trademarks